United States Patent
Chen et al.

(10) Patent No.: US 10,206,768 B2
(45) Date of Patent: Feb. 19, 2019

(54) METHOD FOR TREATING MALE URINARY INCONTINENCE AND A CONTROLLABLE URETHRAL CLAMP

(71) Applicant: UNION HOSPITAL, TONGJI MEDICAL COLLEGE, HUAZHONG UNIVERSITY OF SCIENCE AND TECHNOLOGY, Wuhan, Hubei (CN)

(72) Inventors: Chaohui Chen, Hubei (CN); Huafang Wang, Hubei (CN)

(73) Assignee: UNION HOSPITAL, TONGJI MEDICAL COLLEGE, HUAZHONG UNIVERSITY OF SCIENCE AND TECHNOLOGY, Wuhan (CN)

( * ) Notice: Subject to any disclaimer, the term of this patent is extended or adjusted under 35 U.S.C. 154(b) by 106 days.

(21) Appl. No.: 15/598,272

(22) Filed: May 17, 2017

(65) Prior Publication Data
US 2017/0319318 A1    Nov. 9, 2017

(30) Foreign Application Priority Data
May 20, 2016    (CN) .......................... 2016 1 0340474

(51) Int. Cl.
*A61F 2/02* (2006.01)
*A61F 2/00* (2006.01)
(Continued)

(52) U.S. Cl.
CPC ............ *A61F 2/0031* (2013.01); *A61B 50/30* (2016.02); *A61F 2/0054* (2013.01); *A61B 17/3209* (2013.01); *A61B 2017/0618* (2013.01)

(58) Field of Classification Search
CPC ............................ A61F 2/0031; A61F 2/0054
(Continued)

(56) References Cited

U.S. PATENT DOCUMENTS

| 4,942,886 A | * | 7/1990 | Timmons | ............ A61B 17/132 128/885 |
| 5,336,157 A | * | 8/1994 | Hale | ................. A61B 17/1227 128/843 |

(Continued)

FOREIGN PATENT DOCUMENTS

| CN | 2419951 Y | 2/2001 |
| CN | 203447396 U | 2/2014 |

OTHER PUBLICATIONS

1st Office Action of counterpart Chinese Patent Application No. 201610340474.X dated Apr. 1, 2017.

*Primary Examiner* — John Lacyk (57) ABSTRACT

The present application discloses a method for treating male urinary incontinence, which includes the following steps: 1) male urethral reconstruction surgery, 2) preparation of a urethral clamp, and 3) application of the urethral clamp. The urethral clamp and the surgical treatment of male urinary incontinence are low in medical costs, and no artificial material is implanted into the body. The method and the clamp device have the advantages of accurate urine control effect, simple manipulation of urination, minimal urethral reconstruction surgery, high success rate, and simple operation. It does not affect the sensation of penis and cavernous erection. It does not affect the appearance of penis, and it is easy for patients to accept the method and the clamp device. A controlled urethral clamp for the treatment of male urinary incontinence is also disclosed.

4 Claims, 5 Drawing Sheets

(51) Int. Cl.
*A61B 50/30* (2016.01)
*A61B 17/3209* (2006.01)
*A61B 17/06* (2006.01)

(58) Field of Classification Search
USPC .................. 600/29–32; 128/885, DIG. 25
See application file for complete search history.

(56) References Cited

U.S. PATENT DOCUMENTS

| | | | |
|---|---|---|---|
| 6,349,727 B1 * | 2/2002 | Stewart, Jr. .......... | A61B 17/122 128/885 |
| 6,843,253 B2 * | 1/2005 | Parkes .................. | A61F 2/0054 128/885 |
| D767,761 S * | 9/2016 | Babb ............................ | D24/143 |

* cited by examiner

METHOD FOR TREATING MALE URINARY INCONTINENCE AND A CONTROLLABLE URETHRAL CLAMP

CROSS-REFERENCE TO RELATED APPLICATION

This application claims the benefit of Chinese Patent Application No. 201610340474.X, filed on May 20, 2016, the entire content of which is hereby incorporated by reference.

FIELD OF THE TECHNOLOGY

The present application relates to a method of treating a disease, and more particularly to a method for treating male urinary incontinence, and to a controllable urethral clamp for use in the method for treating male urinary incontinence.

BACKGROUND

Male urinary incontinence usually occurs after trauma or surgery, such as severe pelvic fractures combined with urethral external sphincter injury, etc. However, the most common male urinary incontinence occurs after surgery, such as transurethral resection of prostate, radical prostatectomy, radical resection of bladder, urethral stricture incision, prostate radiotherapy, and congenital malformation and absence of urethral sphincter, and so on.

Transurethral resection of prostate is a standard surgery for treatment of benign prostatic hyperplasia in elderly patients. If the surgical resection technique is not properly mastered or controlled and the urethral sphincter is injured, then real urinary incontinence may occur so that one cannot control the urine and the urine flows out of the urethra automatically. For radical prostatectomy, urinary incontinence may occur when sphincter injury occurs due to huge tumor invasion or resection scope. Radical resection of bladder includes removal of prostate gland. Again, urinary incontinence may occur when sphincter injury occurs due to huge tumor invasion or resection scope.

Urinary incontinence causes great inconvenience to patients. The patients need to wear diapers for a long period of time and cannot leave the house. It has a great impact on the psychological and physiological sides of the patients. It is also an important source of medical disputes and tension between doctors and patients. For young urinary incontinence patients, they would almost lose their courage to work, and would affect their sexual life and even lead to family rupture.

Male urinary incontinence is a worldwide problem in the surgical field. Existing surgical method and equipment cannot completely solve the problem, and the medical costs and complications are very obvious. Severe pelvic fractures combined with urethral external sphincter injury, and a variety of surgeries involving the urethral sphincter are likely to lead to male urinary incontinence. At present, medical treatment of male incontinence and rehabilitation method include (1) anus-lifting exercise and training for recovery of the function of sphincter; (2) male artificial urethral sling implantation; (3) using a penis clamp to completely and closely clamp the entire distal end of the penis; (4) artificial urethral sphincter implantation; (5) reconstructing sphincter with bladder mucosa, and ligament suspension surgery; (6) bladder neck hardening agent injection.

Figure 1:
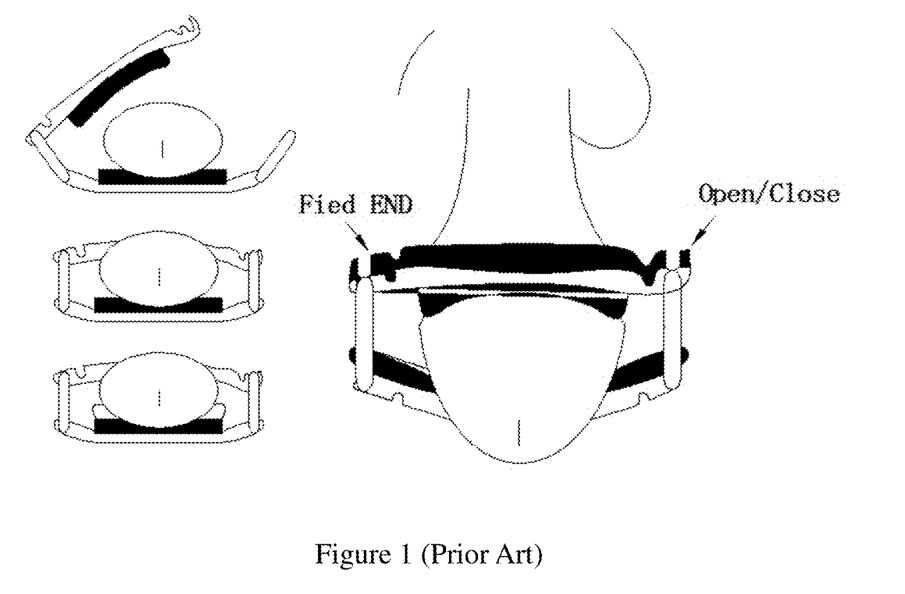
FIG. 1 is a schematic diagram of the operation of a classic penile clamp.
Figure 2:
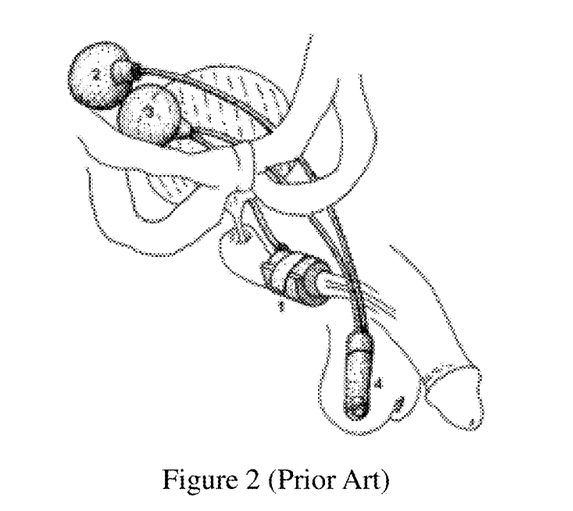
FIG. 2 is a schematic diagram of artificial urethral sphincter implantation.
Figure 3:
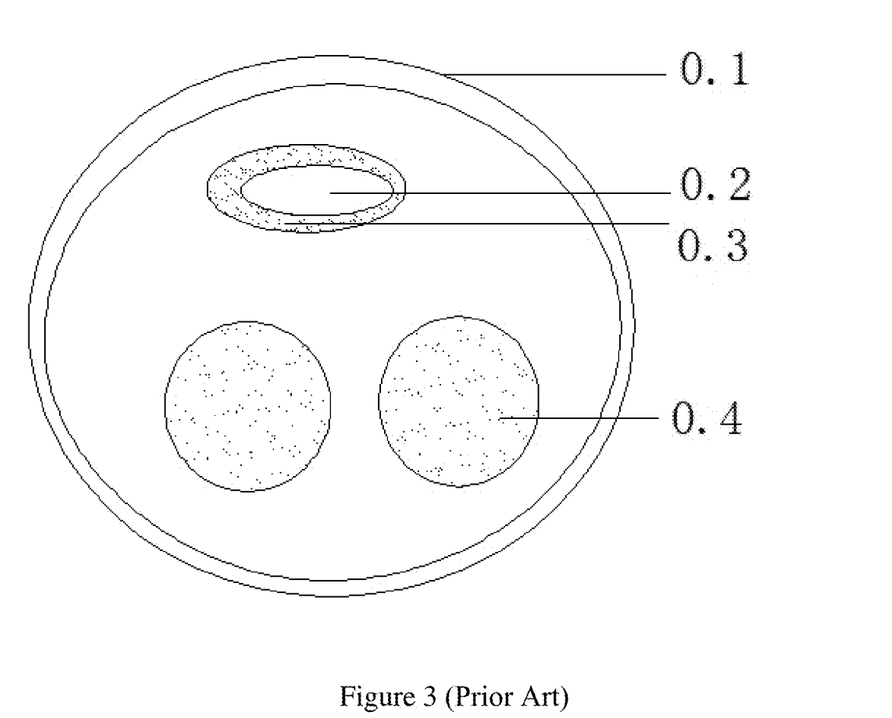
FIG. 3 is a cross-sectional view of the main structure of a penis of a normal person. (the penis ventral side up) (0.1: urethral ventral skin and fascia, 0.2: urethral cavity, 0.3: corpus spongiosum, 0.4: corpus cavernosum)
Figure 4:
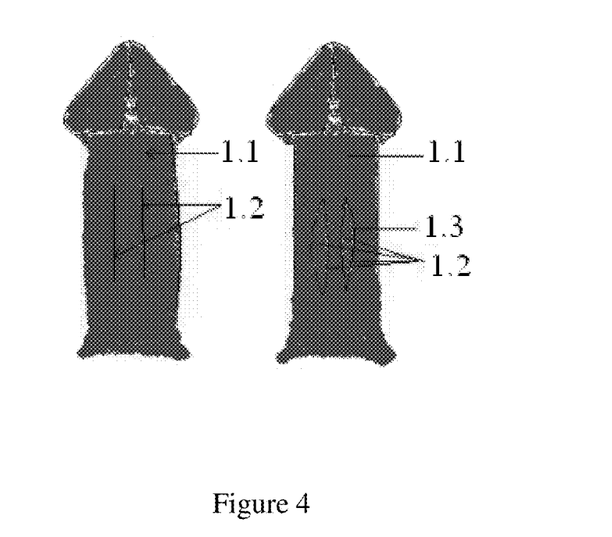
FIG. 4 is a diagram of a penile ventral surgery incision. (1.1: penile ventral skin surface, 1.2: projecting area of the skin incisions at the gap adjacent the corpus spongiosum, 1.3: corpora cavernosa under the penis skin and fascia)
Figure 5:
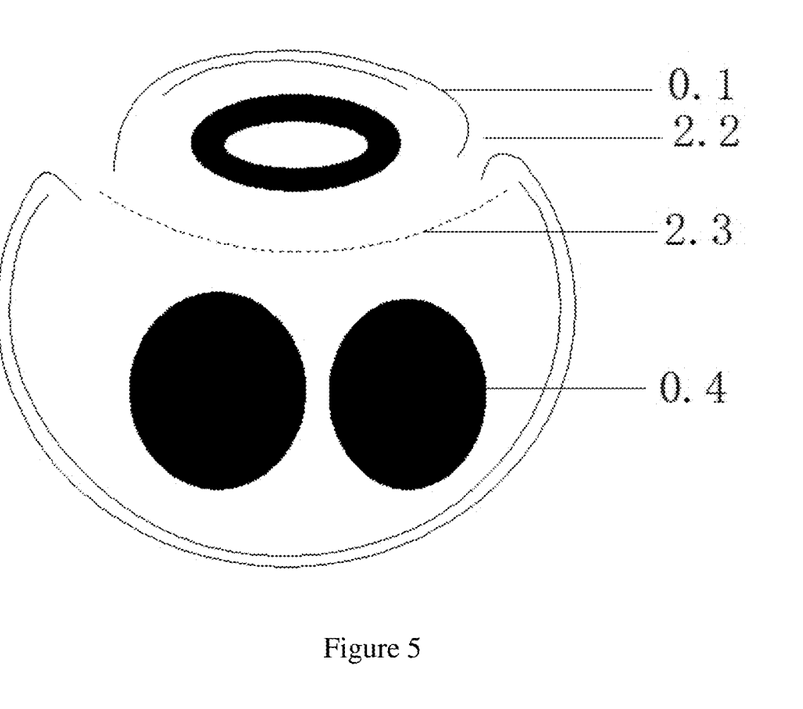
FIG. 5 is a diagram of partial dissociation of the corpus spongiosum and the corpus cavernosum (partial cross section). (0.1: urethral ventral skin and fascia, 2.2: wrap around after dissociation of incision skin, 2.3: partial dissociation interface of the corpus spongiosum and the corpus cavernosum, 0.4: corpus cavernosum)
Figure 6:
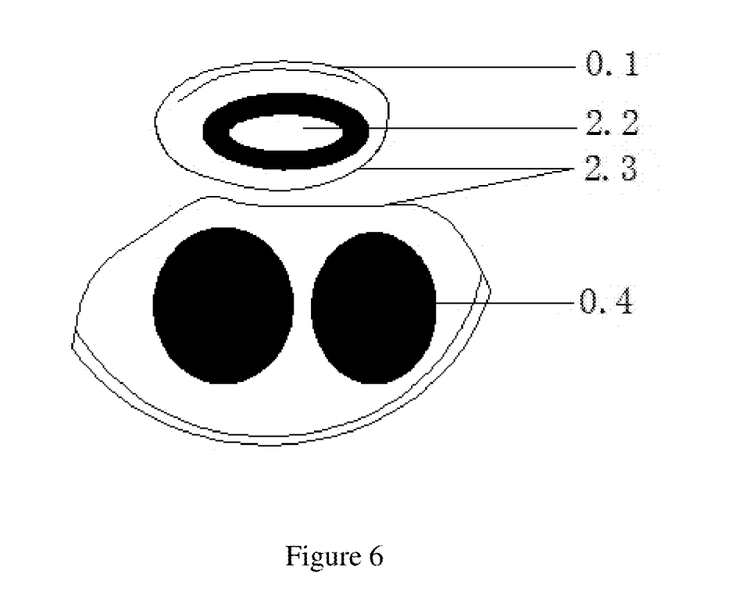
FIG. 6 is a diagram of the corpus spongiosum and the corpus cavernosum after partial dissociation and skin formation (partial cross section). (0.1: urethral ventral skin and fascia, 0.2: urethral cavity, 3.3: skin passing through the gap between the corpus spongiosum and the corpus cavernosum, and wrapping around the corpus spongiosum and the corpus cavernosum, 0.4: corpus cavernosum)
Figure 7:
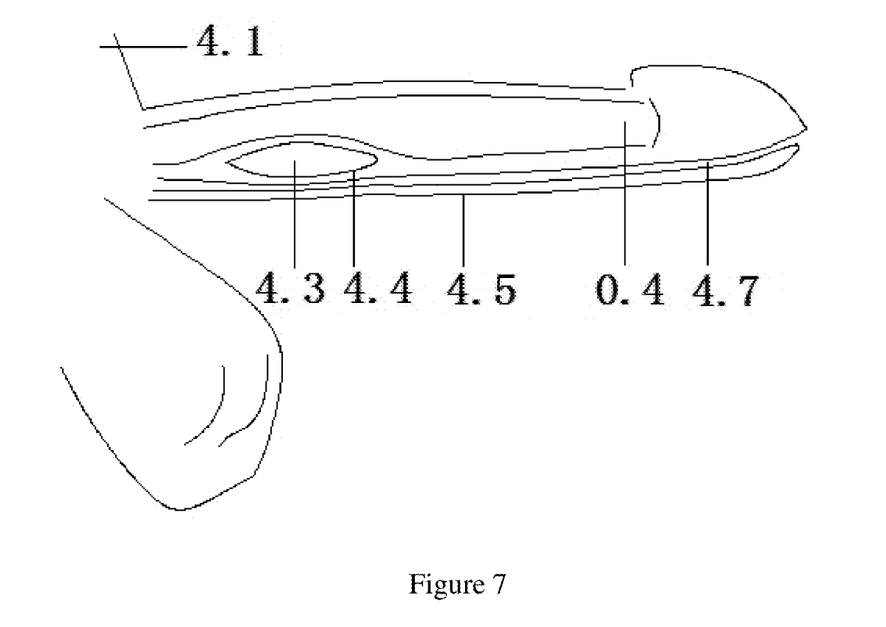
FIG. 7 is a diagram of the corpus spongiosum and the corpus cavernosum after partial dissociation and skin formation (general side view). (4.1: skin of pubic area, 4.2: scrotum, 4.3: separating gap between the corpus spongiosum and the corpus cavernosum, 4.4: skin passing through gap between the corpus spongiosum and the corpus cavernosum, and wrapping around the corpus spongiosum and the corpus cavernosum, 4.5: penile ventral skin, 0.4: corpus cavernosum, 4.7 urethra)

Device and method such as a classic penis clamp where the whole penis is completely clamped (as shown in FIG. 1), and artificial urethral sphincter implantation (complicated device implanted in the human body, complicated surgical operation, high costs, as shown in FIG. 2) have significant defects. It cannot really solve urinary incontinence and can only reach a certain degree of relief. The existing methods for treatment of male urinary incontinence are complicated and have complications, or the structure of the device is complicated, leaving the body prone to infection and rejection.

(1) Anus-lifting exercise and training, and pelvic base biofeedback electrical nerve stimulation: Researches have confirmed that these methods belong to the scope of physiotherapy rehabilitation training. Real urinary incontinence cannot be completely healed by merely muscle training.

(2) Male artificial urethral sling implantation: An artificial material in the form of a patch is implanted in the human body in order to suspend the male urethral bulb and treat urinary incontinence caused by sphincter injury. This method cannot achieve significant urine control for severe real urinary incontinence. The degree of tightness of the sling implantation may lead to complete out of control of urine, or urine cannot be discharged. The implantation of a foreign material in the body may lead to tissue inflammation and possible reject reaction, and is therefore potentially dangerous.

(3) Penile clip: Its working principle is similar to an elastic rubber band. It ties up the entire penis, including corpus spongiosum, corpus cavernosum, skin, nerves, and blood vessels to close the urinary tract and prevent leakage of urine. The tightening band can be released to allow urine to flow out. The penile clip tightly clamps the entire penis, including the basic structure of the penis, such as blood vessels, nerves, fascia, etc. for a long time, and is only released to restore blood flow and feel during urination. This technique can easily lead to disorder of blood circulation at the distal end of the penis, which may lead to numbness of the penis, penile erectile dysfunction, and even tissue necrosis at the distal end of the penis. Long clamping of the entire penis can also lead to complete loss of sexual intercourse ability.

(4) Artificial urethral sphincter implantation: Artificial urethral sphincter implantation is considered to be the gold standard for treatment of urinary incontinence after prostatectomy. However, even experienced doctors still have a failure rate of more than 35%. Furthermore, the method requires the entire device to be implanted in the body by surgery. The surgical process is difficult to master and promote, and is high in medical costs. Foreign object implantation in human body has high chance of infection and rejection.

(5) Reconstruct sphincter with bladder mucosa, and ligament suspension surgery: It has poor surgical results. Urine control is not ideal, and surgical trauma is large.

(6) Bladder neck hardening agent injection: Surgical trauma is not large, but the effect of urine control is poor. Side effects of injection of hardening agent into the human body include local inflammation, tissue necrosis, etc.

The above-mentioned surgical treatments of male urinary incontinence obviously cannot be very effective in solving real male urinary incontinence. The surgical procedures are complex, and surgical trauma is large. These limit the treatment effect on male urinary incontinence patients. They cannot achieve a simple and effective solution to thoroughly solve the problem of male urinary incontinence.

SUMMARY

The first object of the present application is to modify the structure of the male urethra by a small operation, i.e. to propose a method for treating male urinary incontinence, which has the advantages of simple operation, minimal trauma and excellent surgical outcomes, etc.

The second object of the present application is to provide a controllable urethral clamp for the treatment of male urinary incontinence, which can selectively clamp the urethra to achieve urinary continence.

The first object of the present application can be achieved by a method of treating male urinary incontinence, including the steps of:
1) performing a male urethra reconstruction surgery, including the following steps:
    disinfecting a surgical area at a male perineum, and inserting an 18F Foley catheter into a male urethra through an external orifice thereof until reaching a bladder;
    making two incisions in a skin along a longitudinal axis of a penis at a ventral side of a root of the penis near a scrotum portion along two junctions between a corpus spongiosum and two sides of a pair of corpus cavernosum respectively, each of the incisions being 2-3 cm in length, separating a fascia under the skin, and revealing the corpus spongiosum and the corpus cavernosum;
    bluntly separating the corpus spongiosum and the corpus cavernosum until completely dissociating a segment of the corpus spongiosum, and forming a gap between the corpus spongiosum and the corpus cavernosum;
    wrapping the ventral penile skin around the corpus spongiosum, and stitching up the ventral penile skin at the gap to cover the corpus spongiosum;
    dissociating the skin at the two sides of the corpus cavernosum, making the skin at the two sides of the corpus cavernosum slightly loosened, stitching up the skin at the two sides of the corpus cavernosum at the gap;
    covering the skin with a sterile Vaseline dressing after observing that blood supply to the skin closure is fine;
    keeping the catheter for one week, and waiting for the skin incision to heal completely; and
2) applying an urethral clamp to compress the urethra for urinary control, adjusting pressure of the urethral clamp, and pressing the urethra to achieve urine control for different patients with different pressures.

In step 2) of the above method, the urethral clamp is manufactured by the steps of: using a computer-aided design or a 3-dimensional printing method; manufacturing urethral clamps of different sizes according to urethral sizes of patients, the urethral clamp being made of a medical silicone high molecular material by a single casting in a mold, the urethral clamp comprising a first clamp piece (1) and a second clamp piece (2), which are used as a closeable attached assembly.

A method of using the urethral clamp comprising: fastening the first clamp piece and the second clamp piece together by first and second connecting members provided on the first clamp piece and the second clamp piece respectively; clenching first and second handles of the first clamp piece and the second clamp piece to separate first and second elastic plates of the first clamp piece and the second clamp piece respectively; inserting the elastic plate of the first clamp piece or the second clamp piece through the gap; releasing the handles to thereby press the urethra for urine control; and adjusting the distance between the connecting members of the first clamp piece and the second clamp piece to adjust pressing force of the elastic plates on the urethra.

A controllable urethral clamp for treatment of male urinary incontinence is characterized by having a first clamp piece and a second clamp piece, which are used as a closeable attached assembly.

The first clamp piece includes a first plastic elastic plate, a first surface layer of soft sponge medium, a first handle, and a first cylindrical hollow connecting member provided with a central trough, wherein the first plastic elastic plate and the first handle are integrally formed into a Z-shape, an inner concave surface of the first plastic elastic plate is connected with the first surface layer of soft sponge medium, a joining region of the first plastic elastic plate and the first handle is connected with the first cylindrical hollow connecting member.

The second clamp piece include a second surface layer of soft sponge medium, a second plastic elastic plate, a second cylindrical hollow connecting member, a plurality of elastic catching teeth, and a second handle, wherein the second plastic elastic plate is formed integrally with the second handle, an outer convex surface of the second plastic elastic plate is connected with the second surface layer of soft sponge medium, a joining region of the second plastic elastic plate and the second handle is connected with the second cylindrical hollow connecting member, and an outer wall of the second cylindrical hollow connecting member is provided with the plurality of elastic teeth for engaging with the central trough.

In a preferred embodiment, the urethral clamp is made of a high molecular elastomeric polyethylene material, and the first clamp piece and the second clamp piece are formed by a single casting in a mold.

The present method and device are used to reconstruct the urethral structure before surgery. The skin at the root of a penis is cut. The corpus spongiosum is separated from the corpus cavernosum. The penile skin flap is stretched to cover the surgical wound. Finally, the root of the penis is in a form similar to ear piercing that forms an opening for the wearing of an ear-ring. A special urethral clamp is then used to simply clamp or release the corpus spongiosum covered by the skin, and the purpose of control the discharge of urine can be achieved.

The advantages of the present device includes minimal operative trauma, high success rate, and easy to use for patients. It does not affect the sensation of the penis and the erection function of the corpus cavernosum, and artificial material is not implanted into the human body. The clamp device can selectively clamp the urethra to control urinary effect. Manipulation of urination is simple. It does not affect the appearance of the penis, and does not affect erection of the penile corpus cavernosum. Specific advantages are as follows:
(1) The special urethral clamp is easy to manufacture and has a low manufacturing cost; (2) the urethral clamp and treatment of male urinary incontinence involve low medical costs; (3) no artificial material implanted in the human body; (4) urine control effect is exact, and manipulation of urination is simple; (5) trauma of the preoperative urethral surgery is very small, success rate is high, and operation is simple; (6) it does not affect sensation of the penis and function of cavernous erection; (7) it does not affect the appearance of the patient's penis; and (8) easy for patients to accept the method and device.

DETAILED DESCRIPTION

The present method and device will now be described in further detail with reference to the accompanying drawings and specific examples, but they are not to be construed as limiting the scope of protection, and the advantages of the method and device will become more apparent and readily understood.

A method of treating male urinary incontinence is shown in FIGS. 1-7.

1) Pre-Operative Male Urethra Reconstruction Surgery:
(a) disinfecting a surgical area at a male perineum, and inserting an 18F Foley catheter into a male urethra through an external orifice thereof until reaching a bladder; (b) making two incisions in a skin along a longitudinal axis of a penis at a ventral side of a root of the penis near a scrotum portion along two junctions between a corpus spongiosum and two sides of a pair of corpus cavernosum respectively, each of the incisions being 2-3 cm in length, separating a fascia under the skin, and revealing the corpus spongiosum and the corpus cavernosum; (c) bluntly separating the corpus spongiosum and the corpus cavernosum until completely dissociating a segment of the corpus spongiosum and forming a gap between the corpus spongiosum and the corpus cavernosum; (d) wrapping the ventral penile skin around the corpus spongiosum, and stitching up the ventral penile skin at the gap to cover the corpus spongiosum; (e) dissociating the skin at the two sides of the corpus cavernosum, making the skin at the two sides of the corpus cavernosum slightly loosened, stitching up the skin at the two sides of the corpus cavernosum at the gap; (f) covering the skin with a sterile Vaseline gauze after observing that blood supply to the skin is fine; (g) keeping the catheter for a week, and waiting for the skin to heal completely.

2) Manufacturing of Urethral Clamp:
Using a computer-aided design or a 3-dimensional printing method, and manufacturing urethral clamps of different sizes according to urethral sizes of patients. The urethral clamp may be made of a medical silicone high molecular material by a single casting in a mold. The urethral clamp may include a first clamp piece and a second clamp piece, which are used as a closeable attached assembly.

3) Method of Using the Urethral Clamp:
Fastening the first clamp piece and the second clamp piece together by first and second connecting members provided on the first clamp piece and the second clamp piece respectively; clenching first and second handles of the first clamp piece and the second clamp piece to separate first and second elastic plates of the first clamp piece and the second clamp piece respectively; inserting the elastic plate of the first clamp piece or the second clamp piece through the gap; releasing the handles to thereby press the urethra for urine control; and adjusting the distance between the connecting members of the first clamp piece and the second clamp piece to adjust pressing force of the elastic plates on the urethra. This can achieve urine control for different patients with different urethral pressures.

Figure 8:
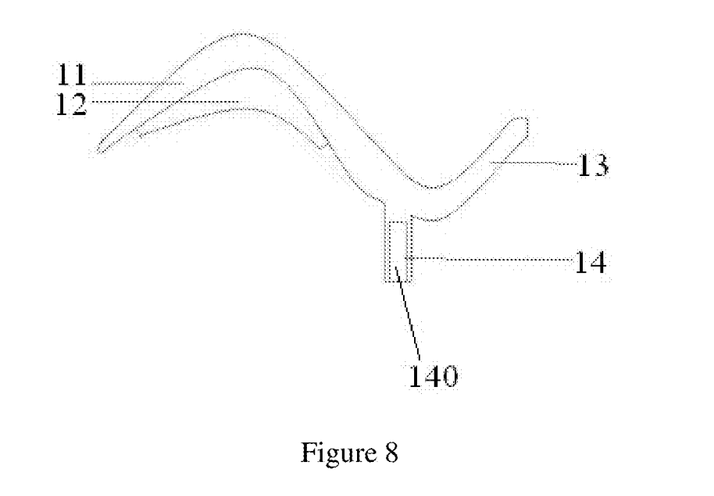
FIG. 8 is a schematic view of one urethral clamp piece.
Figure 9:
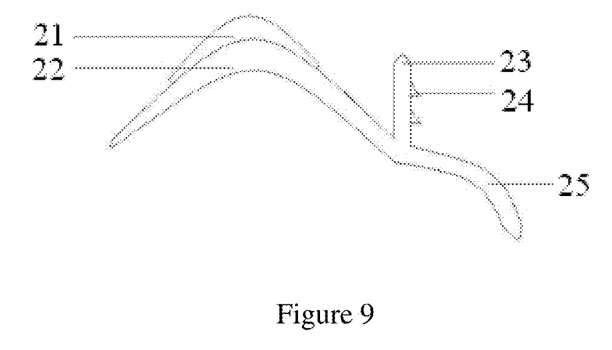
FIG. 9 is a schematic view of another urethral clamp piece.
Figure 10:
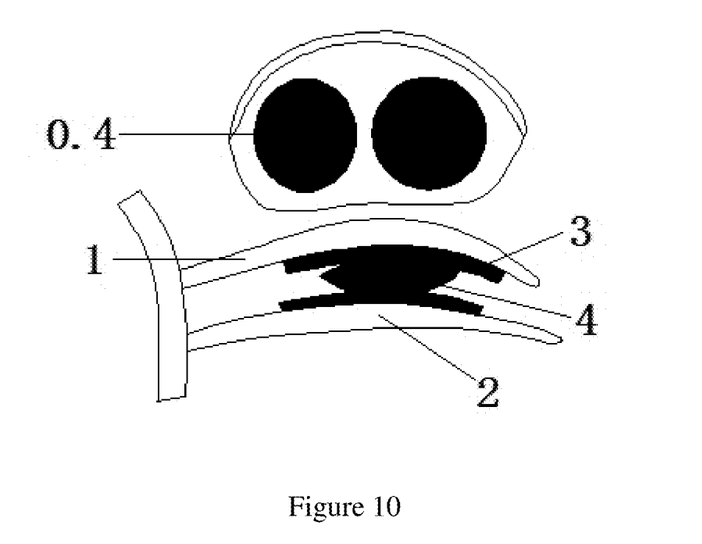
FIG. 10 is a cross-sectional view of the urethral clamp in operation. (1: plastic elastic plate, 2: cylindrical hollow connecting member of the urethral clamp, 3: surface layer of soft sponge medium, 4: press and close the urethra, 0.4: corpus cavernosum)

FIGS. 8-10 show a controllable urethral clamp for treatment of male urinary incontinence. The urethral clamp includes a first clamp piece 1 and a second clamp piece 2, which are used as a closeable attached assembly.

The first clamp piece 1 may include a first plastic elastic plate 11, a first surface layer of soft sponge medium 12, a first handle 13, and a first cylindrical hollow connecting member 14 formed with a central trough 140. The first plastic elastic plate 11 and the first handle 13 are integrally formed into a Z-shape, an inner concave surface of the first plastic elastic plate 11 is connected with the first surface layer of soft sponge medium 12, a joining region of the first plastic elastic plate 11 and the first handle 13 is connected with the first cylindrical hollow connecting member 14.

The second clamp piece 2 may include a second surface layer of soft sponge medium 21, a second plastic elastic plate 22, a second cylindrical hollow connecting member 23, a plurality of elastic catching teeth 24, and a second handle 25. The second plastic elastic plate 22 is formed integrally with the second handle 25, an outer convex surface of the second plastic elastic plate 22 is connected with the second surface layer of soft sponge medium 21, a joining region of the second plastic elastic plate 22 and the second handle 25 is connected with the second cylindrical hollow connecting member 23, and an outer wall of the second cylindrical hollow connecting member 23 is provided with the plurality of elastic teeth 24 for engaging with the central trough 140. The urethral clamp may be made of a high molecular elastomeric polyethylene material, and the first clamp piece 1 and the second clamp piece 2 are formed by a single casting in a mold.

The present device and technology can completely change the current status of treatment of male urinary incontinence. It can ideally solve the problem of male urinary incontinence. It is the world's first pioneer in the field.

Evaluation standard of the efficacy of the device: As reported in the literature, the standard of healing of urine incontinence is that the patient no longer needs to use urine pad, or a reduction of consumption to 1-2 urine pads per day, as well as the number of urine pad consumed, and life quality scoring and satisfaction of urine control by urethral clamps (feel of satisfaction is divided into: very satisfied, satisfied, average, dissatisfied and very dissatisfied) according to International Prostate Scoring System (IPSS).

The urethral clamp may be made of non-toxic high molecular elastomeric polyethylene material, a single mold casting, and two pieces which are used as a closeable attached assembly.

Other features that are not described in detail are existing technology.

What is claimed is:

1. A method of treating male urinary incontinence, comprising the steps of:
   1) performing a pre-operative male urethra reconstruction surgery, comprising the steps of:
      disinfecting a surgical area at a male perineum, and inserting an 18F Foley catheter into a male urethra through an external orifice thereof until reaching a bladder;
      making two incisions in a skin along a longitudinal axis of a penis at a ventral side of a root of the penis near a scrotum portion along two junctions between a corpus spongiosum and two sides of a pair of corpus cavernosum respectively, each of the incisions being 2-3 cm in length, separating a fascia under the skin, and revealing the corpus spongiosum and the corpus cavernosum;
      bluntly separating the corpus spongiosum and the corpus cavernosum until completely dissociating a segment of the corpus spongiosum, and forming a gap between the corpus spongiosum and the corpus cavernosum;
      wrapping the ventral penile skin around the corpus spongiosum, and stitching up the ventral penile skin at the gap to cover the corpus spongiosum;
      dissociating the skin at the two sides of the corpus cavernosum, making the skin at the two sides of the corpus cavernosum slightly loosened, stitching up the skin at the two sides of the corpus cavernosum at the gap;
      covering the skin closure with a sterile Vaseline dressing after observing that blood supply to the skin closure is fine;
      keeping the catheter for one week, and waiting for the skin incision to heal completely; and
   2) applying an urethral clamp to compress the urethra for controlling urine, adjusting pressure of the urethral clamp, and pressing the urethra to achieve urine control for different patients with different urethral pressures.

2. The method of treating male urinary incontinence according to claim 1, wherein, in step 2), the urethral clamp is manufactured by the steps of: using a computer-aided design or a 3-dimensional printing method; manufacturing urethral clamps of different sizes according to urethral sizes of patients, the urethral clamp being made of a medical silicone high molecular material by a single casting in a mold, the urethral clamp comprising a first clamp piece (1) and a second clamp piece (2), which are used as a closeable attached assembly; and
   a method of using the urethral clamp comprising: fastening the first clamp piece (1) and the second clamp piece (2) together by first and second connecting members provided on the first clamp piece (1) and the second clamp piece (2) respectively; clenching first and second handles of the first clamp piece (1) and the second clamp piece (2) to separate first and second elastic plates of the first clamp piece (1) and the second clamp piece (2) respectively; inserting the elastic plate of the first clamp piece (1) or the second clamp piece (2) through the gap; releasing the handles to thereby press the urethra for urine control; and adjusting distance between the connecting members of the first clamp piece (1) and the second clamp piece (2) to adjust pressing force of the elastic plates on the urethra.

3. A controllable urethral clamp for treatment of male urinary incontinence, comprising a first clamp piece (1) and a second clamp piece (2), which are used as a closeable attached assembly;
   the first clamp piece (1) comprising a first plastic elastic plate (11), a first surface layer of soft sponge medium (12), a first handle (13), and a first cylindrical hollow connecting member (14) formed with a central trough (140), wherein the first plastic elastic plate (11) and the first handle (13) are integrally formed into a Z-shape, an inner concave surface of the first plastic elastic plate (11) is connected with the first surface layer of soft sponge medium (12), a joining region of the first plastic elastic plate (11) and the first handle (13) is connected with the first cylindrical hollow connecting member (14);
   the second clamp piece (2) comprising a second surface layer of soft sponge medium (21), a second plastic elastic plate (22), a second cylindrical hollow connecting member (23), a plurality of elastic catching teeth (24), and a second handle (25), wherein the second plastic elastic plate (22) is formed integrally with the second handle (25), an outer convex surface of the second plastic elastic plate (22) is connected with the second surface layer of soft sponge medium (21), a joining region of the second plastic elastic plate (22) and the second handle (25) is connected with the second cylindrical hollow connecting member (23), and an outer wall of the second cylindrical hollow connecting member (23) is provided with the plurality of elastic teeth (24) for engaging with the central trough (140).

4. The controllable urethral clamp for treatment of male urinary incontinence according to claim 3, wherein the urethral clamp is made of a high molecular elastomeric polyethylene material, and the first clamp piece (1) and the second clamp piece (2) are formed by a single casting in a mold.

* * * * *